United States Patent [19]

D'Herbecourt et al.

[11] Patent Number: 6,146,762
[45] Date of Patent: Nov. 14, 2000

[54] MODIFIED POROUS SILICA, PROCESS FOR ITS MANUFACTURE AND ITS USE IN PAINTS AND AS A CARRIER PIGMENTS AND DYES

[75] Inventors: Bruno D'Herbecourt; Yves Lermat; Michael Werth, all of Bernay; Olivier Julien, Ste Foy-les-Lyons, all of France

[73] Assignee: Elf Atochem S.A., Puteaux, France

[21] Appl. No.: 09/061,241

[22] Filed: Apr. 16, 1998

[30] Foreign Application Priority Data

Apr. 29, 1997 [FR] France .................................. 97-05273

[51] Int. Cl.⁷ ...................................................... B32B 5/16
[52] U.S. Cl. ............................................ 428/404; 428/407
[58] Field of Search .................................. 428/402, 403, 428/404, 407

[56] References Cited

U.S. PATENT DOCUMENTS

| | | |
|---|---|---|
| 3,421,931 | 1/1969 | Reverand . |
| 3,954,678 | 5/1976 | Marquisse . |
| 4,223,070 | 9/1980 | Hahn et al. ............................... 428/407 |
| 4,330,519 | 5/1982 | Takahashi et al. ....................... 423/335 |
| 4,590,052 | 5/1986 | Chevallier et al. ...................... 423/335 |
| 4,874,594 | 10/1989 | Chevallier ................................ 423/335 |
| 5,230,953 | 7/1993 | Tsugeno et al. ......................... 428/331 |
| 5,342,876 | 8/1994 | Abe et al. ................................ 524/493 |
| 5,614,176 | 3/1997 | Persello ..................................... 424/57 |

FOREIGN PATENT DOCUMENTS

| | | |
|---|---|---|
| 0 303 530 | 8/1988 | European Pat. Off. . |
| 2 619 385 | 2/1989 | France . |
| 4 424 775 | 1/1996 | Germany . |
| 57-147434 | 9/1982 | Japan . |
| 57-200425 | 12/1982 | Japan . |
| 62-074970 | 4/1987 | Japan . |

OTHER PUBLICATIONS

French Search Report dated Nov. 10, 1997.

*Primary Examiner*—H. Thi Le
*Attorney, Agent, or Firm*—Smith, Gambrell & Russell

[57] ABSTRACT

The invention relates to porous silicas in which the pores are at least partially filled with polyamide resins. They can be employed as additives to liquid paints, as carriers for pigments and/or dyes, as antiblocking agents for folded or wound films made of olefinic material and in cosmetic, pharmaceutical and/or dermatological compositions.

9 Claims, No Drawings

MODIFIED POROUS SILICA, PROCESS FOR ITS MANUFACTURE AND ITS USE IN PAINTS AND AS A CARRIER PIGMENTS AND DYES

FIELD OF THE INVENTION

The invention relates to the field of porous silicas and particularly of modified porous silicas usable especially as additives to liquid paints and as carriers for pigments and/or dyes.

BACKGROUND OF THE INVENTION

In order to improve the abrasion resistance and the scratch resistance of paints, various additives are added, which include especially silica powders and/or polyamide powders.

However, the use of silica powders is limited, on the one hand, because of the sedimentation which takes place within the paints into which they are introduced and, on the other hand, because of their low resistance to crayoning (ability of a paint-covered surface to be marked after being rubbed with an object, especially metallic; this phenomenon being all the more visible when the paint is light in tint). To improve the dispersion of the silica powders and to limit their sedimentation within paints, this being in order to obtain better stability of the said paints, it has been proposed to modify the silica powders, for example by addition of polyethylene waxes, but the mixture is tricky to produce and this technical solution does not produce any improvements insofar as the other weak points referred to above are concerned.

Polyamide (PA) powders exhibit excellent abrasion and scratch resistance properties but their presence in paints generally does not improve the resistance to crayoning either. In addition, milling polyamide resins to the desired particle size—of the order of a few tens of $\mu$m—is sometimes found to be tricky when the said PA powders are obtained by polycondensation. PA powders of the desired particle size can be obtained directly without subsequent grinding, by anionic polymerization and especially according to the process described in Patent Application FR 2 619 385 or in Patent EP 303 530.

The paints containing silica powder and polyamide powder, described in Kansai Paint Co's Patent Application JP62074970 offer a compromise which is correct but still insufficient insofar as the abrasion, scratch and crayoning resistance is concerned.

DESCRIPTION OF THE INVENTION

Applicant has now found modified silicas which can be used especially as additives for paints (liquid or otherwise) and as carriers for dyes or pigments.

The modified silicas according to the invention simultaneously improve the abrasion, scratch and crayoning resistance of the paints in which they are incorporated. They consist of porous silica in which the pores are at least partially filled with polyamide resins and whose PA/silica mass ratio is between 1/100 and 2/1.

The porous silicas from which the modified silicas according to the invention originate have a pore volume of between 0.4 and 2 ml/g, an absorptivity, measured according to DIN standard ISO 787/V of between 100 and 350 g of oil/100 g of silica of mean particle diameter of between 0.5 and 150 $\mu$m, preferably between 1 and 20 $\mu$m. Such porous silicas can be prepared by reaction of sulphuric acid with a sodium silicate and then washing, grinding and drying of the powders obtained. It is possible to employ as raw material porous silica powders which have undergone an organic coating such as, for example, coating with the aid of polyethylene waxes.

Uncoated porous silicas are preferred by Applicant.

Porous silicas, coated or otherwise, are marketed especially by Grace under the mark Syloid and by J. Crossfield & Sons.

The polyamide resins which occupy at least a portion of the volume of the pores of the modified silicas according to the invention are semicrystalline PAs whose melting point or range is in general between 80 and 275°; they are in general prepared from diacids and diamines and/or from aminoacids and/or from lactams, among which 11-aminoundecanoic acid will be mentioned very particularly.

Another subject-matter of the present invention is two processes for the preparation of the modified silicas according to the invention.

The first process developed by Applicant consists in solubilizing the monomers of the polyamide resin in an aqueous or hydroalcoholic solution containing an alcohol which has from 1 to 4 carbon atoms. For the solubilization of the said monomers it is sometimes necessary to operate at temperatures which are higher than the ambient temperature but lower than the boiling temperature of the solvent. Once the solubilization of the monomers has been completed, the porous silica is added in a quantity such that all the solution is absorbed by the silica powder. The solvent is removed by placing, for example, the silica powder in an oven or in a drier in the usual operating conditions for the removal of water or of a water/alcohol mixture (high temperatures, more or less deep vacuum).

The polymerization of the PAs is next carried out by heating the powder to temperatures allowing the PA monomer(s) to melt, typically between 100 and 260° C. for a period which can vary according to the chosen polymerization temperature and is in general between a few minutes and a few hours. Using techniques which are known per se, the polymerization reaction can be accelerated by applying a vacuum to the polymerization reactor so as to remove the water of polycondensation which has formed. During the polymerization of the PAs it is possible to add various additives (heat and UV stabilizers, plasticizers and the like), catalysts (preferably chosen from phosphorus oxides), chain limiters generally chosen from mono- and diacids and mono- and diamines, optical brighteners and the like.

At the end of the polymerization of the PAs the modified silica according to the invention is obtained which has substantially the same particle size as the starting porous silica.

The second process developed by Applicant can only be used in the case of PAs whose monomers are solid at ambient temperature and are capable of being reduced to powder, for example by milling. This second process consists in dry-blending the monomers in powder form and the porous silica at the ambient temperature and then performing the polymerization of the PA monomers by heating the above mixture to a temperature which is higher than the melting temperature of the said monomers.

At the end of the polymerization the modified silica according to the invention is obtained which has substantially the same particle size as the starting porous silica.

Another subject-matter of the present invention is various uses of the modified silica described above.

They can be employed as additives to paints to improve their resistance to abrasion, to scratches and to crayoning. In general, they are incorporated in a proportion of 0.5 to 10% of the total weight of the paint. Like silica powders, the silicas according to the invention impart a matting effect to the paint in which they are incorporated, i.e. their presence allows the gloss of the paint to be appreciably decreased.

They can be incorporated into liquid paints in an organic phase or in aqueous phase or into paints in powder form.

The liquid paints can be applied to the substrates to be coated using known techniques, such as the application with a varnisher directly or in "reverse" by spraying with the aid of a gun with mixed air or without air, by coating on a belt or coil coating, and the like.

The paints in powder form can be applied by various techniques, among which there may be mentioned spraying with the aid of an electrostatic gun and immersion of the substrate to be coated in a fluidized bath.

The paints can be applied onto substrates of diverse nature and shape. The substrates most commonly employed are metallic (steel, iron, aluminium, alloys and the like), but it is also possible to coat substrates made of wood, glass, paper and of composite, layered or laminated materials.

Before coating with the aid of the paint the substrate may undergo one or more surface treatments (degreasing, flaming, corona treatment, action of a plasma, and the like) intended to improve the anchoring of the paint; the substrate may be precoated with the aid of an adhesion primer before coating with the paint.

The modified silica according to the invention can also be employed as antiblocking agent intended to prevent the adhesive bonding to themselves of films based on (co) polyolefins or olefin blends, which are folded or wound on reels, like the silica powders of the prior art (see, for example, DE 4 424 775).

The modified silica according to the invention can moreover be employed as carrier for incorporating pigments, dyes, stabilizers, antioxidants and/or anti-UV agents and other usual additives which are often in the form of very fine and very volatile powders, and this has the effect of very appreciably limiting the volatility of these products when they are being handled and being incorporated in diverse compositions in liquid or solid form.

Finally, it can be used for the preparation of products for cosmetic, dermatological and/or pharmaceutical use, such as powders, eye shadows, lipsticks, foundations, products for cleansing or removing make-up, lotions, care creams, shampoos, dentifrices and the like.

EXAMPLES

Examples 1 to 7

Preparation of Modified Silica

Example 1

In a 500-ml pear-shaped Rotavapor® round bottom flask are placed 30 g of silica of 5 μm mean particle size, of pore volume 1.8 ml/g and of absorptivity, measured according to DIN ISO standard 787/V equal to 320 g of oil/100 g of silica, marketed by Grace under the trade name Syloid® ED 5, together with 33 g of 11-aminoundecanoic acid (All).

The flask is placed under a nitrogen purge, immersed in a bath of silicone oil heated to 240° C., and rotated at a speed of the order of 1 rev/min.

After 3 min the temperature in the flask reaches 220° C., that is to say higher than the melting temperature of 11-aminoundecanoic acid, and a release of water is noted, which means that the polycondensation reaction has already started.

After 30 min of reaction, when the temperature of the reaction mixture has stabilized at 234° C., the flask is cooled while the purging with nitrogen is maintained and an agglomerate-free powder of mean particle size equal to 5 μm is recovered.

The inherent viscosity of the PA extracted from the modified silica, measured in a solution containing 0.5% of PA in m-cresol at 25° C., is 0.94.

Example 2

By repeating the operating conditions of Example 1 and starting from the same starting materials but in modified proportions (30 parts by weight of All and 70 parts of silica), modified silica powder according to the invention is prepared with a PA/silica mass ratio of 30/70.

Example 3

By repeating the operation conditions of Example 1 and starting from the same starting materials but in modified proportions (10 parts by weight of All and 90 parts of silica), modified silica powder according to the invention is prepared with a PA/silica mass ratio of 10/90.

Example 4

From the same starting materials as in Example 1 and in similar operating conditions (only the polymerization time is modified and is taken to 1 h). A powder is obtained with the same particle size as the starting silica powder, agglomerate-free and in which the polyamide, once extracted from the modified silica, has an inherent viscosity of 1.22.

Example 5

In operating conditions similar to those of Example 1 (polymerization temperature: 253° C.; polymerization time: 20 min), a modified silica is prepared from the same silica as that in Example 1, from hexanediamine and from adipic acid in a mass ratio (PA-6,6 monomers)/silica of 50/50. A modified silica powder according to the invention is obtained, with the same particle size as the starting silica powder but which exhibits approximately 15% by weight of agglomerates.

Example 6

In operating conditions similar to those of Example 1 (polymerization temperature: 230° C.; polymerization time: 30 min) a modified silica is prepared from the same silica as that in Example 1 and from 6-aminohexanoic acid in a 6-aminohexanoic acid/silica mass ratio of 50/50. One third of the 6-aminohexanoic acid is converted to ε-caprolactam and distils during the preparation of the modified silica. A powder of the same particle size as the starting silica powder is obtained, but this powder is highly agglomerated.

Example 7

In operating conditions which are similar to those in Example 1 an attempt is made to prepare a modified silica from the same silica as that in Example 1 and from dodecalactam in a dodecalactam/silica mass ratio of 50/50. Sublimation of the dodecalactam is noted and a silica powder is obtained from which no PA-12 is extracted.

The experiment is repeated, an organic acid being added to try to trigger the polymerization, but no improvement is observed.

Examples 8 to 10

Use of Modified Silica as Paint Additive

A paint is prepared by preparing a dispersion of the various constituents with the aid of a high-speed disperser in which glass beads can be incorporated to facilitate dispersion of the constituents. Once the dispersion is produced, one or more solvents are optionally added to obtain a paint with the desired paint viscosity.

| Dispersion: | (parts by weight) |
|---|---|
| solution of polyurethane resin (polyester with IDPI hydroxyl ends/e-caprolactone) of viscosity, measured at 25° C. according to DIN standard 51757, of 1.06, in a solvent consisting of xylene and ethylglycol acetate (2/1 mixture by volume) (PU concentration: 60% by weight) | 74.45 |
| mixture of equal volumes of butyldiglycol acetate and of Solvesso ® 200 (hydrocarbon mixture marketed by Esso, the boiling point of which is between 224 and 285° C.) | 9.60 |
| surfactant | 0.25 |
| wetting agent | 0.60 |
| solution of dibutyltin laurate in butyldiglycol acetate (dibutyltin laurate concentration: 40% by weight) | 0.75 |
| additive improving the resistance to abrasion, to scratches and to crayoning | 4.75 |
| Viscosity adjustment: mixture of equal volumes of butyldiglycol acetate and of Solvesso ® 200 (hydrocarbon mixture marketed by Esso, the boiling point of which is between 224 and 285° C.) | 9.60 |
| Total | 100 |

A Bonderized® aluminium panel of 0.8 mm thickness is covered with the aid of a white primer applied with a bar and then crosslinked for 40 s in an oven maintained at 340° C. (the maximum temperture reached by the substrate being 240° C.). The substrate thus coated is next immersed in water and then dried in the surrounding air.

The above paint is then applied with a bar onto the substrate in order to be crosslinked in the same conditions as those used for the application of the primer.

A composite material is obtained, consisting:

of a primer of thickness equal to approximately 5 μm of a layer of surface coating of thickness between 15 and 20 μm of an aluminium substrate of 0.8 mm thickness.

Example 8

Comparative

As indicated above, a paint is prepared in which the additive improving the resistance to abrasion, to scratches and to crayoning is the porous silica marketed by Grace under the name Syloid® ED 5 and a substrate is covered with the aid of this paint using the procedure indicated above.

Example 9

Comparative

As indicated above, a paint is prepared in which the additive improving the resistance to abrasion, to scratches and to crayoning is a mixture of 70 parts by weight of porous silica Syloid® ED 5 and 30 parts of PA-11 powder marketed by the Applicant under the name Rilsan® D30 of 30 μm mean particle size and a substrate is covered with the aid of this paint using the procedure indicated above.

Example 10

As indicated above, a paint is prepared in which the additive improving the resistance to abrasion, to scratches and to crayoning is the modified silica of Example 1 and a substrate is covered with the aid of this paint using the procedure indicated above.

Abrasion resistance

The abrasion resistance of the coatings of Examples 8 to 10 is tested.

The abrasion resistance of the coatings is measured with the aid of Taber abrasimeter fitted with a CS 10 grinding wheel for a 500 g load.

The results are combined in Table 1.

TABLE 1

| Example No. | 8 | 9 | 10 |
|---|---|---|---|
| Loss in weight after 800 cycles (mg) | 17.3 | 15.3 | 10.8 |
| Loss in weight after 1000 cycles (mg) | ∞ | 18.8 | 13.9 |

∞ complete destruction of the coating

Storage stability

The storage stability of the paints of Examples 8 to 10 is measured by storing 100 g of each of them in a 250-ml glass bottle for a period of 48 h. Any deposit formed is evaluated with the aid of a spatula. The results are combined in Table 2.

TABLE 2

| Example No. | 8 | 9 | 10 |
|---|---|---|---|
| Deposit type | very hard deposit, paint difficult to rehomogenize | slight sedimentation, paint easy to rehomogenize | slight sedimentation, paint easy to rehomogenize |

Examples 11 to 14

Use of Modified Silica in a Satin-finish Varnish (Acrylic Emulsion Base)

a—Preparation of the varnish

A matting paste is prepared first of all by dispersing the ingredients of Table 3 for 20 min with high-speed stirring.

TABLE 3

| Ingredient | Manufacturer | Function | Parts by weight | Parts by volume |
|---|---|---|---|---|
| Deionized water | | | 91.7 | 91.7 |
| Mergal ® K6N | Riedel-de Haën | fungicidal agent | 14.8 | 14.8 |
| 1,2- | | | 341.9 | 328.8 |

TABLE 3-continued

| Ingredient | Manufacturer | Function | Parts by weight | Parts by volume |
|---|---|---|---|---|
| Propanediol Butyl-diglycol | | coalescence solvent | 171.4 | 170.4 |
| Texanol | Eastman | coalescence solvent | 136.6 | 143.8 |
| AMP ® 90 | Angus Chemie GmbH | amine neutralizer | 14.8 | 15.6 |
| Coatex ® Rheo 2000 ® | Coatex | acrylic thickener | 28.0 | 26.4 |
| Additive* | | | 180.0 | 94.7 |
| BYK ®-024 | Byk Chemie GmbH | antifoam agent | 20.8 | 23.1 |
| Total | | | 1000.0 | 919.3 |

A portion of the matting paste is next dispersed with the ingredients shown in Table 4 for 20 min at a speed of 2000 rev/min.

TABLE 4

| Ingredient | Manufacturer | Function | Parts by weight | Parts by volume |
|---|---|---|---|---|
| Repolem ® 2141 | Elf Atochem S.A. | acrylic emulsion | 837.5 | 797.6 |
| Matting paste | | | cf Tab 5 | |
| Deionized water | | | 24.5 | 24.5 |
| Coatex ® Rheo 2000 ® | Coatex | acrylic thickener | 12.0 | 11.3 |
| Troysan ® Polyphase ® AF3 | TroyChemical Corp | fungicidal agent | 3.0 | 2.7 |
| BYK ®-024 | Byk Chemie GmbH | antifoam agent | 2.0 | 2.1 |
| Total | | | 1000.0 | 919.3 |

The contents of reinforcing additive and the proportion of matting paste in the varnishes of Examples 11 to 14 are shown in Table 5.

TABLE 5

| Example | Varnish | 11 | 12 | 13 | 14 |
|---|---|---|---|---|---|
| Additive content (% by weight) | — | 2.2 | 2.2 | 2.4 | 1.1 |
| Matting paste (% by weight) | 0 | 12.1 | 12.1 | 24.2 | 6.05 |

The varnishes thus obtained (Examples 11 to 14) have a relative density of 1.05, a pH of 8.5 and a solids content of 41.8% by weight.

The matting and reinforcing additive of Example 11 is Syloid® ED 50 (silica coated with an organic agent, of 5 μm mean particle size, pore volume of 1.8 ml/g and absorptivity, measured according to DIN ISO standard 787/V, equal to 300 g of oil/100 g of silica).

The matting and reinforcing additive of Examples 12 and 13 is the modified silica of Example 1.

The matting and reinforcing additive of Example 14 is a porous polyamide powder of 5 μm mean particle size, with an apparent specific surface of 10 m²/g, marketed by the Applicant under the name Orgasol® 2001 UD Nat 1.

The viscosities (ICI, Brookfield) according to ISO standard 2884, the Taber abrasion resistance according to NF standard T 30-015 and the gloss of the varnishes according to ISO standard 2813 are evaluated and the results are combined in Table 6.

TABLE 6

| Example | Varnish | 11 | 12 | 13 | 14 |
|---|---|---|---|---|---|
| ICI viscosity at $10^4$ s$^{-1}$ (mPa s) | 64 | 92 | 83 | 96 | 70 |
| Brookfield viscosity (mPa s), spindle 3, speed 20 | 380 | 1340 | 1620 | 3130 | 720 |
| Transparency* | 10 | 3 | 5 | 3 | 2 |
| 60° gloss in % | 83.5 | 27 | 43.5 | 26.5 | 49.5 |
| 20° gloss in % | 67 | 5 | 12.8 | 5 | 19 |
| Taber abrasion, (500 g load) | — | 30.5 | 26.3 | 24.9 | 25.7 |
| Taber abrasion, (1000 g load) | — | 72.1 | 78.4 | 69.2 | 71.7 |
| Dispersibility | — | medium | good | good | poor |

Examples 15 to 19

Use of Modified Silica in a Paint in the Form of Powder as Pigment Carrier

A modified silica is prepared from 50 parts by weight of Syloid® ED 5, 40 parts of All and 10 parts of black pigment (carbon black marketed under the name Monarch 800) by repeating the procedure of Example 1.

A powder of 5 μm mean particle size is obtained, of which 18 parts are mixed dry per 1000 parts of PA-11 powder of mean particle size of approximately 100 μm, marketed by the Applicant Company under the name Rilsan® natural grade T Nat 2 P in a Henschel mixer for 100 s at a speed of 900 rev/min.

The powder thus obtained is placed in a fluidized bed in application conditions which are usual for the dip-coating of PA-based powders (powder fluidized with compressed air passing through the porous slab of the fluidized bed). A 10×10×0.3 cm steel panel preheated for 10 min in an oven maintained at 330° C. is immersed in the fluidized bath for 6 s as soon as it leaves the oven. The appearance of the film is assessed visually and its gloss is measured according to ISO standard 2813.

By way of comparison, powder paints are prepared from the same PA-11 to which unmodified silica Syloid® ED 5 and carbon black Monarch 800 are added (1.8 parts per 1000 parts of PA-11) as a dry mix.

Furthermore, the paint formulations of Examples 15 to 19 contain, per 1000 parts of PA, 3.5 parts of antioxidant and spreading agent.

10×10×0.3 cm steel panels are coated with the aid of these paints and their appearance and their gloss are evaluated as indicated above. The results are combined in Table 7.

TABLE 7

| Example No. | Matting agent | Parts per 1000 of PA | Film appearance | 60° gloss in % |
|---|---|---|---|---|
| 16 | modified silica Example 15 | 18 | correct "rough" feel | 26 |

TABLE 7-continued

| Example No. | Matting agent | Parts per 1000 of PA | Film appearance | 60° gloss in % |
|---|---|---|---|---|
| 17 | Syloid ® ED 5 | 2 | correct | 40 |
| 18 | Syloid ® ED 5 | 5 | very many pits | 40 |
| 19 | Syloid ® ED 5 | 10 | not in film form | not measurable |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Silica comprising a pore volume of between 0.4 and 2 ml/g, an absorptivity, measured according to DIN ISO standard 787/V of between 100 and 350 g of oil/100 g of silica, mean particle diameter of between 0.5 and 150 $\mu$m; modified with polyamide resins whose monomers are solid at ambient temperature, and obtained by dry mixing of the polyamide monomers reduced to powder and of the silica at ambient temperature, followed by the polymerization of the said monomers whereby a porous silica is obtained in which the pores are at least partially filled with polyamide resins.

2. Silica according to claim 1, wherein the Polyamide-monomer/silica mass ratio is between 1 to 100 and 2 to 1.

3. Silica according to claim 1, wherein the monomers of the polyamide resins are amino acids or mixtures of diamines and diacids.

4. Method for treating a substrate comprising adding to varnishes and/or paints in liquid form in organic phase or in aqueous phase or in solid form the modified silica according to claim 1.

5. Method for preparation of paints and cosmetic compositions comprising adding the modified silica according to claim 1 as carrier for incorporating compounds which are in finely divided form and/or volatile in liquid and/or solid compositions.

6. Method for treating fibers comprising using the modified silica according to claim 1 as antiblocking agent for films based on (co)polyolefins or olefin blends, folded or wound on reels.

7. Method for the preparation of cosmetic, dermatological and/or pharmaceutical products comprising the modified silica according to claim 1.

8. Process for the preparation of the modified silica of claim 1, comprising solubilizing at least one polyamide monomer in an aqueous or hydroalcoholic solution and then adding the porous silica, removing the solvent and polymerizing the at least one polyamide.

9. Process for the preparation of the modified silica of claim 1, wherein the polyamide monomers being in powder form and mixing the porous silica dry at ambient temperature and then performing the polymerization of the polyamide monomers.

* * * * *